United States Patent [19]
Giselbrecht et al.

[11] Patent Number: 5,898,076
[45] Date of Patent: Apr. 27, 1999

[54] PROCESS FOR PREPARING 1-PYRUVYL-L-PROLINE

[75] Inventors: Karlheinz Giselbrecht, Pasching; Curt Zimmermann, Mauthausen, both of Austria

[73] Assignee: DSM Chemie Linz GmbH, Austria

[21] Appl. No.: 09/129,994

[22] Filed: Aug. 6, 1998

[30] Foreign Application Priority Data

Aug. 6, 1997 [AT] Austria ..................... 1319/97
Nov. 12, 1997 [AT] Austria ..................... 1910/97

[51] Int. Cl.⁶ ............... C07D 207/08; C07D 207/06
[52] U.S. Cl. ................. 548/533; 548/579; 548/535
[58] Field of Search .................... 548/579, 533, 548/535

[56] References Cited

U.S. PATENT DOCUMENTS 5,424,454  6/1995  Burbaum et al. .............. 548/533

FOREIGN PATENT DOCUMENTS 0 048 159  3/1982  European Pat. Off. .
WO91/04985  4/1991  WIPO .

OTHER PUBLICATIONS

Soai et al., Diastereoselective Reduction of Chiral . . . , J. Chem. Soc. Perkin Trans. 1 (4) 769–772., Dec. 1985.

N. Krit et al., translation from *Khimiki–farmatsevitcheskii Zhurnal*, 25 (7), 46–49 (Jul. 1991).

G. Jou et al., *J. Org. Chem.*, 62 (2), 354–366 (1997).

*Primary Examiner*—Johann Richter
*Assistant Examiner*—Dominic Keating
*Attorney, Agent, or Firm*—Wenderoth, Lind & Ponack, L.L.P.

[57] ABSTRACT

Process for preparing N-pyruvyl-L-proline by reaction of L-proline with methyl pyruvate dimethyl ketal in the presence of an alkali metal alkoxide, subsequent acid hydrolysis and extraction of 1-pyruvyl-L-proline.

8 Claims, No Drawings

PROCESS FOR PREPARING 1-PYRUVYL-L-PROLINE 1-pyruvyl-L-proline (1-(1,2-dioxopropyl)-L-proline; 76391-12-3) is a useful intermediate in the synthesis of dipeptides and/or polypeptides, for example of those belonging to the class of the N-carboxyalkyldipeptide inhibitors of ACE (angiotensin-converting enzyme).

Because of this, several variants for the preparation of 1-pyruvyl-L-proline have already been described in the literature. Thus, 1-pyruvyl-L-proline (Pyr-Pro-OH) is obtained, for example, according to Jou. G et al, J. Org. Chem., Vol. 62, No. 2, 1997 p. 354–366 by reaction of L-proline benzyl ester hydrochloride with pyruvic acid in the presence of diethanolamine (DIEA), 1-hydroxybenzotriazole (HOBT) and dicyclohexylcarbodiimide (DCC) with a subsequent release of the acid by hydrogenation using hydrogen over Pd/C.

The disadvantage of this reaction is in particular the low yield of 36% of the ester obtained in the first reaction step, the total yield of Pyr-Pro-OH consequently also not being very high. Furthermore, the ester has to be isolated from the reaction mixture and purified prior to the release of the acid.

According to Krit N. A. et al, Khim, Farm. Zh 25 (1991), 1, p. 44–46 (& Pharm. Chem. J. (Engl. translation) 25 (1991) 7, p. 482–485), L-proline benzyl ester is reacted with pyruvyl chloride in DMF and $SOCl_2$ in the presence of triethylamine, and the acid is subsequently released as before by hydrogenation using hydrogen over Pd/C. In this variant, the intermediate ester is again obtained in a poor yield of 40%, in spite of a 100% excess of acyl chloride, so that the total yield in this process is likewise not very high. Furthermore, the ester here also has to be isolated and purified prior to the release of the acid.

It was therefore an object of the present invention to provide a process for preparing Pyr-Pro-OH which ensures a high total yield of Pyr-Pro-OH without isolation and purification of the intermediate formed.

Surprisingly, this object could be achieved by a one-pot reaction with subsequent extraction of the end product.

The present invention thus provides a process for preparing 1-pyruvyl-L-proline which comprises reacting L-proline with methyl pyruvate dimethyl ketal in the presence of an alkali metal alkoxide in an organic solvent and subsequently carrying out an acid hydrolysis of the ketal formed, and isolating 1-pyruvyl-L-proline from the reaction mixture by extraction with an organic solvent.

In the process according to the invention, L-proline is initially reacted with methyl pyruvate dimethyl ketal in the presence of an alkali metal alkoxide. The dimethyl ketal which serves as starting material can be prepared easily on an industrial scale and in high yields, for example by reaction of methyl pyruvate, which is commercially available in high purity, with methanol under acid catalysis ($H_2SO_4$, HCl, p-TsOH, $H_3PO_4$, acid ion exchangers, etc.) and removal of the water of reaction (for example using orthoformic ester) by chemical means or distillatively with recycling of the methanol.

The two starting materials here are preferably employed in equimolar amounts. However, it is also possible to employ a slight excess of the dimethyl ketal.

Suitable alkali metal alkoxides are sodium $C_1$–$C_{10}$-alkoxide, potassium $C_1$–$C_{10}$-alkoxide or lithium $C_1$–$C_{10}$-alkoxide $C_1$–$C_{10}$ alkoxides are for example, methoxide, ethoxide or tert-butoxide, etc. Preference is given to using sodium methoxide. Sodium methoxide can be employed as a solid or as a 30% strength methanolic solution, which is commercially available. The reaction is carried out in the presence of from 1.5 to 3 mol equivalents of alkali metal alkoxide. Preference is given to adding from 1.8 to 2.5, in particular 2, mol equivalents of alkali metal alkoxide. Suitable organic solvents are, for example, $C_1$–$C_4$-alcohols such as, for example, methanol, ethanol, i-propanol, esters such as, for example, methyl acetate, ethyl acetate, etc., toluene, ethers such as, for example, dioxane, THF or methyl tert-butyl ether (MtBE), etc. Preference is given to using dioxane, THF or methanol. Addition of a solubilizer may be required, for example of methanol if MtBE is used.

The reaction temperature is the reflux temperature of the reaction mixture, which depends on the solvent used.

The reaction mixture is stirred at reflux temperature until the reaction has ended, the end of the reaction is monitored gas chromatographically, for example. Preference is given to stirring the reaction mixture for some time after the reaction has ended.

Subsequently, water is added to the reaction mixture, resulting in a phase separation if a water-immiscible solvent is used. If two phases are present, the organic phase is discarded and only the aqueous phase is used further. The subsequent acid hydrolysis is carried out at temperatures of from 15 to about 50° C., preferably at room temperature.

By addition of an inorganic or organic acid, a pH between 1 and 4, preferably between 1 and 2, is set. Suitable inorganic acids are, for example, $H_2SO_4$, $H_3PO_4$, HCl, etc. Suitable organic acids are, for example, p-toluenesulfonic acid, formic acid, acetic acid, etc. Preference is given to using inorganic acids, in particular $H_2SO_4$.

The reaction mixture is stirred for about 0.5 to 15 hours, preferably 1 to 3 hours, to complete the cleavage of the ketal.

Any solid that may be present is separated off prior to the subsequent isolation of Pyr-Pro-OH, for example by filtration with suction, filtration, etc.

To isolate Pyr-Pro-OH, the reaction mixture is preferably concentrated and subsequently extracted with an organic solvent. Suitable extractants are, for example, ethyl acetate, methyl tert-butyl ether (MtBE), diethyl ether, toluene, etc. Preference is given to using ethyl acetate and MtBE. If appropriate, a pH of about 7 is set prior to the extraction, for example by addition of NaOH, to remove any unreacted starting material from the reaction mixture, for example if an excess of dimethyl ketal is used.

The purity of Pyr-Pro-OH is monitored during the extraction by means of thin-layer chromatography, gas chromatography or by HPLC. Once an appropriate purity is obtained, the extractant is distilled off. By the process according to the invention, Pyr-Pro-OH is obtained in yields of up to 90% in a simple manner by a one-pot reaction with subsequent extraction.

EXAMPLE 1

A mixture of 11.5 g (0.1 mol) of L-proline, 14.8 g (0.1 mol) of methyl pyruvate dimethyl ketal,. 10.8 g (0.2 mol) of sodium methoxide and 200 ml of dioxane was stirred at reflux temperature (97–101° C.) for 5 h. 100 ml of $H_2O$ were subsequently added, and a pH of 1.0 was set using $H_2SO_4$ (1:1). The reaction mixture was stirred for another about 3 hours at room temperature, and the resulting solid was then filtered off with suction. The filtrate was concentrated to half its volume and extracted repeatedly with ethyl acetate. Distillative removal of ethyl acetate gave 16.4 g of residue.

Yield: 16.4 g of 1-pyruvyl-L-proline (=90% of theory)

EXAMPLE 2

A mixture of 11.5 g (1 mol) of L-proline, 14.8 g (1 mol) of methyl pyruvate dimethyl ketal, 10.8 g (0.2 mol) of sodium methoxide and 200 ml of methyl tert-butyl ether was heated to reflux temperature (57° C.). In order to dissolve the remaining solid, 5 ml of methanol were added and the mixture was stirred at reflux temperature for 3 h. 100 g of $H_2O$ were subsequently added, as a result of which the remaining solid dissolved and two phases formed. A pH of 5.8 was then set using $H_2SO_4$ (1:1), the organic phase was discarded and the aqueous phase was adjusted to a pH of 1.0 using $H_2SO_4$ (1:1).

The aqueous phase was stirred at 50° C. for another 3 h, concentrated from 150 ml to 80 ml and adjusted to pH 7.0 using 2N NaOH.

The mixture was extracted two times with ethyl acetate, the pH was adjusted to 1.3, again by using $H_2SO_4$ (1:1), and the mixture was extracted another three times with 200 ml of ethyl acetate each time and the ethyl acetate was subsequently distilled off under reduced pressure.

Yield 11.0 g of 1-pyruvyl-L-proline (yellow oil, approximately 60% of theory)

We claim:

1. A process for preparing N-pyruvyl-L-proline, which comprises reacting L-proline with methyl pyruvate dimethyl ketal in the presence of an alkali metal alkoxide in an organic solvent and subsequently carrying out an acid hydrolysis of the ketal formed, and isolating 1-pyruvyl-L-proline from the reaction mixture by extraction with an organic solvent.

2. The process as claimed in claim 1, wherein the alkali metal alkoxide used is sodium $C_1$–$C_{10}$-alkoxide, potassium $C_1$–$C_{10}$-alkoxide or lithium $C_1$–$C_{10}$-alkoxide.

3. The process as claimed in claim 1, wherein the alkali metal alkoxide used is sodium methoxide.

4. The process as claimed in claim 1, wherein from 1.5 to 3 mol equivalents of alkali metal alkoxide are added.

5. The process as claimed in claim 1, wherein equimolar amounts of L-proline and methyl pyruvate dimethyl ketal are employed.

6. The process as claimed in claim 1, wherein the reaction of L-proline and methyl pyruvate dimethyl ketal is carried out at the reflux temperature of the reaction mixture.

7. The process as claimed in claim 1, wherein the acid hydrolysis is carried out at from 15 to 50° C.

8. The process as claimed in claim 1, wherein a pH between 1 and 4 is set for the acid hydrolysis by addition of an inorganic or organic acid.

* * * * *